US00PP36670P2

(12) United States Plant Patent
Koot

(10) Patent No.: US PP36,670 P2
(45) Date of Patent: May 13, 2025

(54) ***BUDDLEJA* PLANT NAMED 'Botex 011'**

(50) Latin Name: *Buddleja davidii*
Varietal Denomination: Botex 011

(71) Applicant: Johannes Adrianus Maria Koot, Kaatsheuvel (NL)

(72) Inventor: Johannes Adrianus Maria Koot, Kaatsheuvel (NL)

(73) Assignee: BOTANIC EXPERIENCE B.V., Kaatsheuvel (NL)

( * ) Notice: Subject to any disclaimer, the term of this patent is extended or adjusted under 35 U.S.C. 154(b) by 0 days.

(21) Appl. No.: 18/912,725

(22) Filed: Oct. 11, 2024

(51) Int. Cl.
*A01H 5/02* (2018.01)
*A01H 6/00* (2018.01)

(52) U.S. Cl.
USPC ..... Plt./242
CPC ..... *A01H 6/00* (2018.05)

(58) Field of Classification Search
USPC ..... Plt./242
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Buddleja* plant named 'Botex 011' that is characterized by its very compact, dense, and a neat and naturally rounded plant habit, its flowers that are light pink in color, its suitability for growing in small containers, and its quick flowering with a very floriferous blooming habit.

3 Drawing Sheets

Botanical classification: *Buddleja davidii.*
Variety denomination: 'Botex 011'.

CROSS-REFERENCE TO RELATED APPLICATIONS

This application is related to a European Community Plant Variety Office (CPVO) Plant Breeder's Rights Application No. 2023/1786 filed on Sep. 13, 2023, under 35 U.S.C. 119(f), the entire contents of which is incorporated by reference herein. The Applicant received the information for the Plant breeders' rights application directly from the Inventor. This application is also co-pending with a U.S. Plant Patent Applications filed for plants derived from the same breeding program that are entitled *Buddleja* Plant Named 'Botex 005' (U.S. Plant Pat. No. 34,703) and *Buddleja* Plant Named 'Botex 008' (U.S. Plant patent Ser. No. 18/824,902), *Buddleja* Plant Named 'Botex 009' (U.S. Plant patent Ser. No. 18/884,264), *Buddleja* Plant Named 'Botex 010' (U.S. Plant patent Ser. No. 18/912,712), *Buddleja* Plant Named 'Botex 012' (U.S. Plant patent Ser. No. 18/912,730), *Buddleja* Plant Named 'Botex 013' (U.S. Plant patent Ser. No. 18/912,731).

BACKGROUND OF THE INVENTION

The present invention relates to a new and distinct cultivar of *Buddleja davidii* will be referred to hereafter by its cultivar name, 'Botex 011'. 'Botex 011' is a new shrub grown for use as an ornamental landscape plant and as a container plant.

The new cultivar of *Buddleja* is a selection from an ongoing breeding program conducted by the Inventor in Kaatsheuvel, The Netherlands with the goal of creating new cultivars of *Buddleja* with very neat and compact plant habits with suitability for growing in small containers combined with unique vibrant flower colors and floriferous blooming habits.

The Inventor made a cross in July of 2019 between unnamed and unpatented proprietary plants in the Inventor's breeding program; reference no. 18-008-01 as the female parent and reference no. 18-027-01 as the male parent. The Inventor selected 'Botex 011' in August of 2022 as a single unique plant amongst the seedlings that resulted from the above cross.

Asexual propagation of the new cultivar was first accomplished by the Inventor using stem cuttings in Kaatsheuvel, The Netherlands in 2022. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Botex 011' as a unique cultivar of *Buddleja.*

1. 'Botex 011' exhibits a very compact, dense, and a neat and naturally rounded plant habit.
2. 'Botex 011' exhibits flowers that are light pink in color.
3. 'Botex 011' exhibits suitability for growing in small containers.
4. 'Botex 011' exhibits quick flowering with a very floriferous blooming habit.

The female parent of 'Botex 011' differs from 'Botex 011' in having smaller and shorter inflorescences, slightly darker leaf color, and flowers that are purple-blue in color. The male parent of 'Botex 011' differs from 'Botex 011' in having flowers that are blue- purple in color, much longer inflorescences, and a taller plant height. 'Botex 011' can be compared to the *Buddleja* cultivars 'Pink Delight' (not patented) and 'Botex 005'. 'Pink Delight' differs from 'Botex 011' in having a taller plant height, a more open plant habit, inflorescences that are less compact and longer, and flowers that are slightly darker pink in color. 'Botex 005' differs from 'Botex 011' in having a less dwarf plant habit.

'Botex 011' can also be compared to the co-pending cultivars of *Buddleja*, 'Botex 008', 'Botex 009', 'Botex 010', 'Botex 012', and 'Botex 013'. 'Botex 008' differs from 'Botex 011' in having flowers that are magenta purple in color and in being taller in height. 'Botex 009' differs from 'Botex 011' in having flowers that are fuchsia pink in color. 'Botex 010' differs from 'Botex 011' in having flowers that are dark, vibrant purple in color. 'Botex 012' differs from 'Botex 011' in having flowers that are light violet blue in color. 'Botex 013' differs from 'Botex 011' in having flowers that are white with orange centers in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by 27East, Dummen Orange, Cool Plants, Floral Daily, Bill Moore & Co., Ball Seed, National Garden Bureau, Visions Pictures, University of Georgia Trial Gardens, Garden Center Magazine, Baldur-Netherland, Plantenkwekerij Vechtdal, Dobrepole, Sweet Garden, and Zahradnictvi-spomysl.

BRIEF DESCRIPTION OF THE DRAWINGS

The accompanying color photographs illustrate the overall appearance and distinct characteristics of the new *Buddleja*. The photographs were taken of a one-year-old plant as grown in a greenhouse in a 19-cm container in Kaatsheuvel, The Netherlands.

The photograph in FIG. 1 provides a side view of the overall plant habit of 'Botex 011' in bloom.

Figure 1:
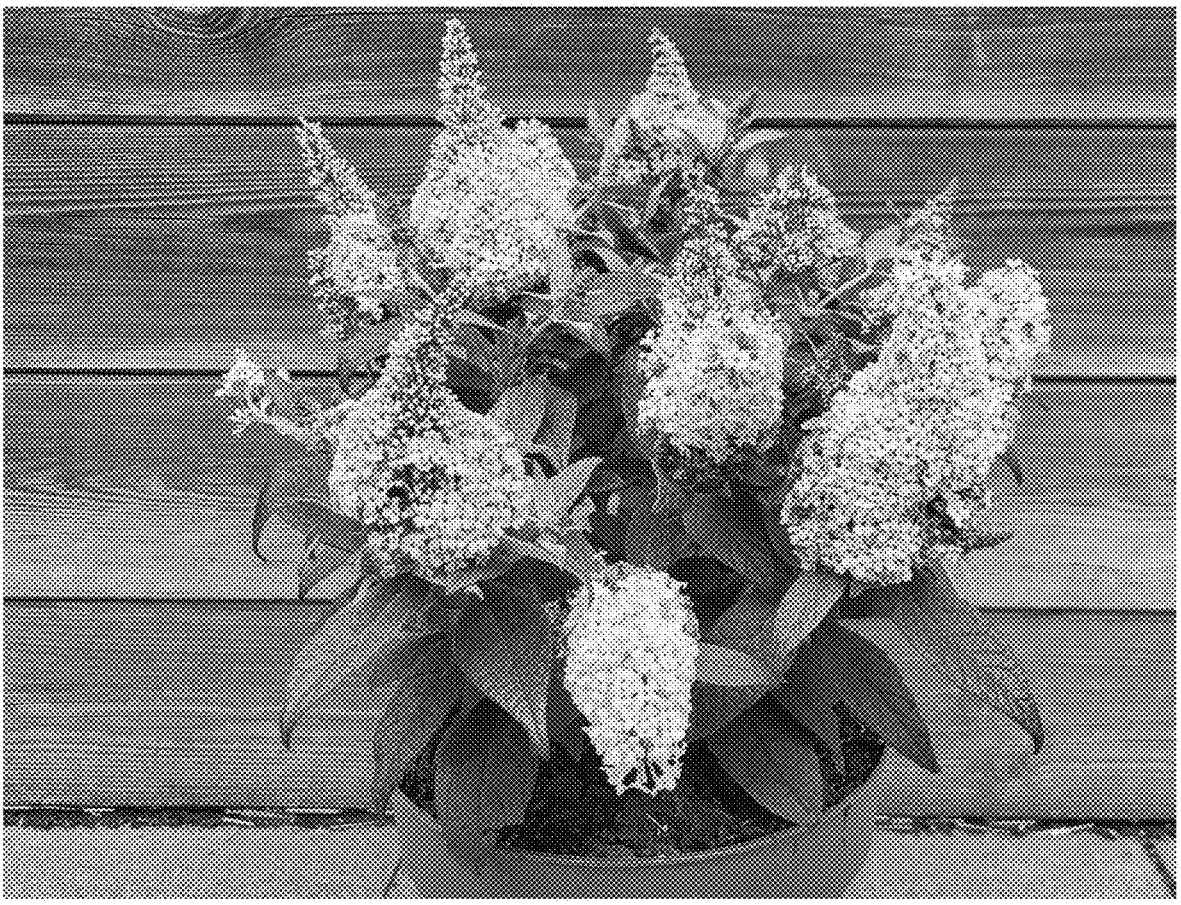
Figure 2:
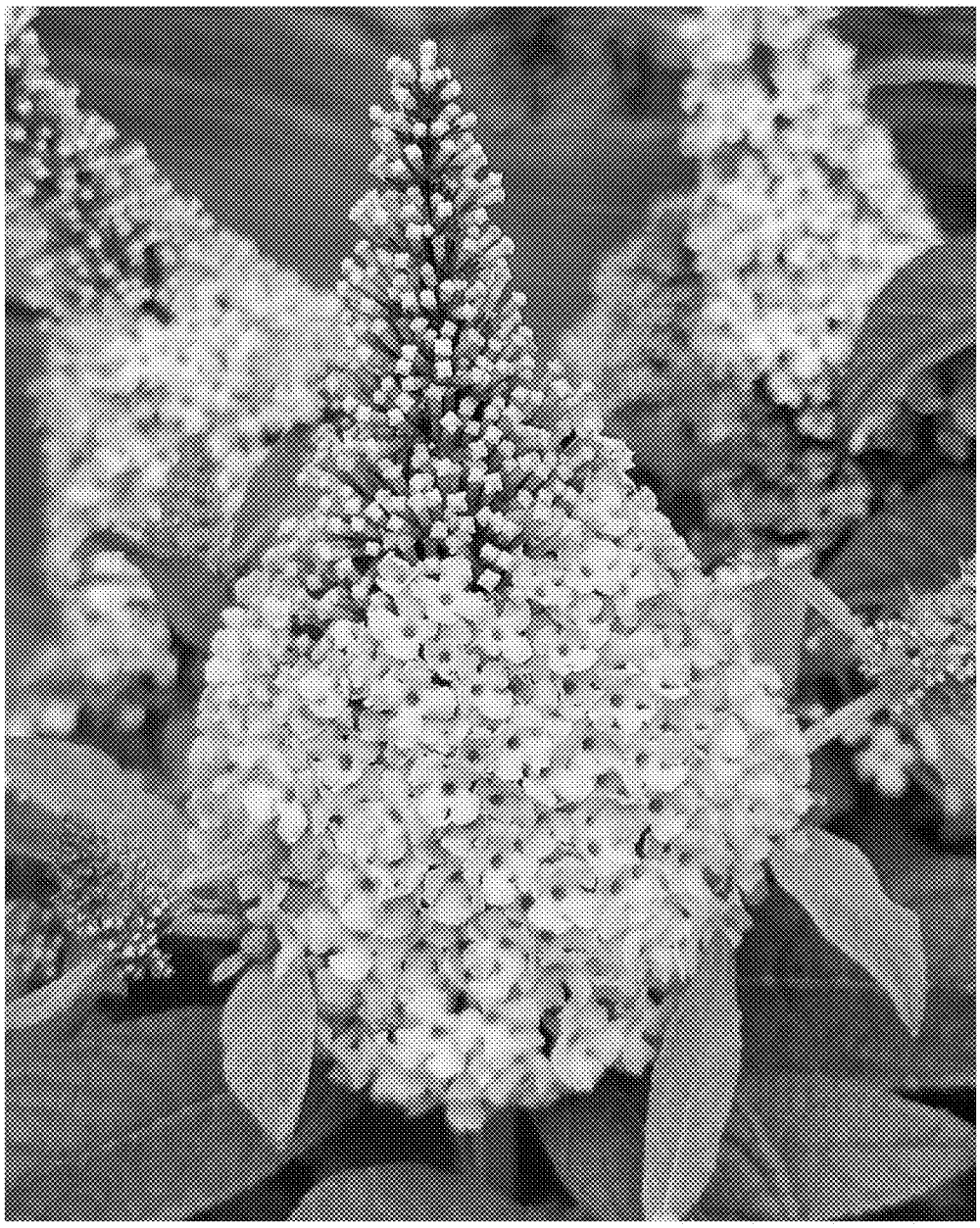

The photograph in FIG. 2 provides a close-up view of an inflorescence of 'Botex 011'.

Figure 3:
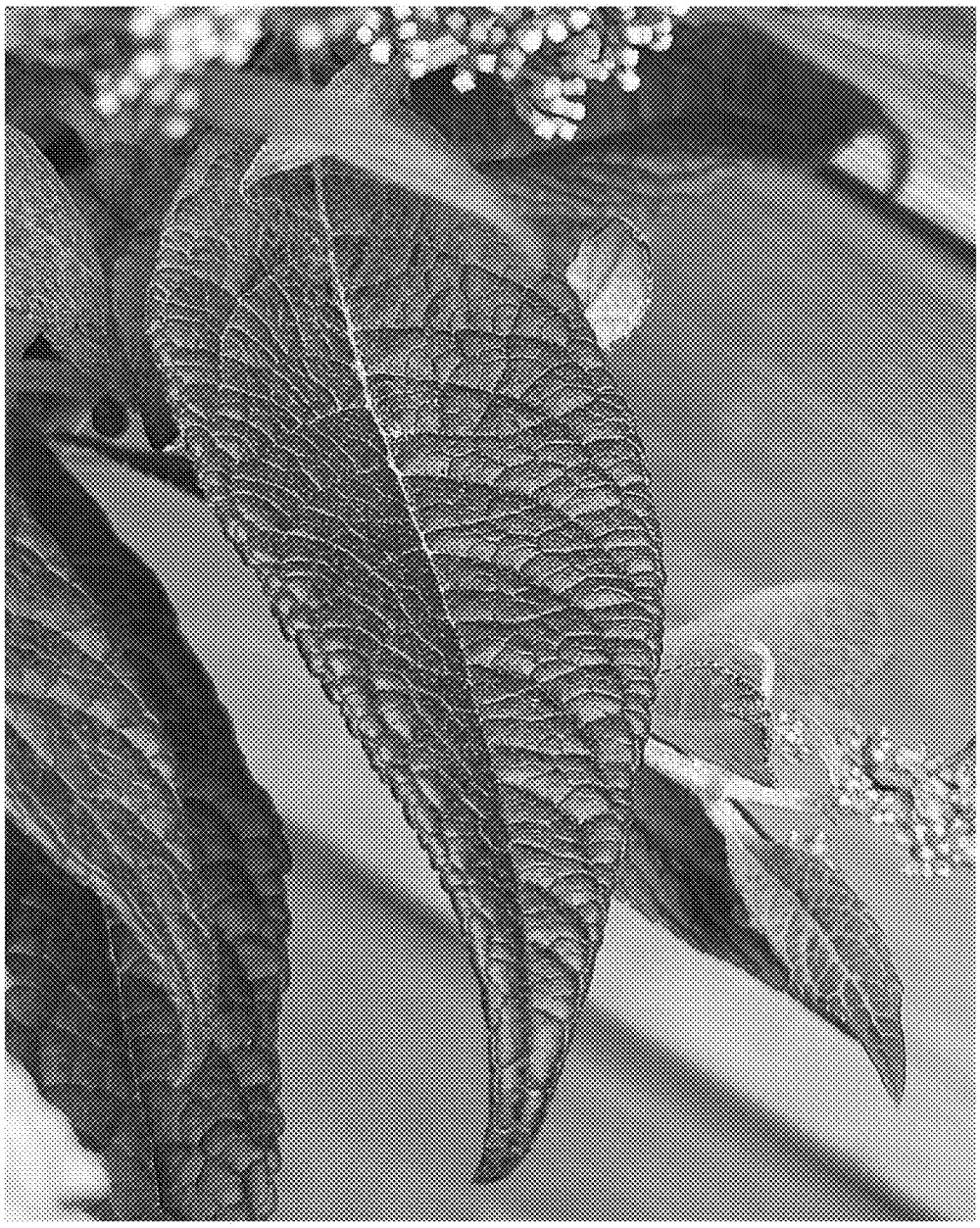

The photograph in FIG. 3 provides a close-up view of a leaf of 'Botex 011'.

The colors in the photographs are as close as possible with the photographic and printing technology utilized and the color values cited in the Detailed Botanical Description accurately describe the colors of the new *Buddleja*.

DETAILED BOTANICAL DESCRIPTION

The following is a detailed description of one-year-old plants as grown in a greenhouse in 19-cm containers in Kaatsheuvel, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—July to October in The Netherlands.

*Plant type.*—Deciduous perennial shrub.

*Plant habit.*—Very compact, upright and naturally rounded, dense.

*Plant size.*—An average of 27 cm in height and 36 cm in width as a one-year-old plant grown in a container and reaches 50 cm in height and in spread as grown in the landscape.

*Cold hardiness.*—At least in U.S.D.A. Zone 5.

*Diseases and pests.*—No susceptibility and resistance to diseases or pests has been observed.

*Propagation.*—Stem cuttings.

*Root description.*—Fibrous.

*Root development.*—4 to 5 weeks to initiate roots and 6 to 7 weeks to fully root as a young plant in a P9 container.

*Growth rate.*—Vigorous, quick finishing.

Branch description:

*Branch shape.*—Quadrangular.

*Branch color.*—Young stems; 145B, mature and older woody stems; 199A.

*Branch strength.*—Strong.

*Branch size.*—Up to 20 cm in length and 4 mm in diameter.

*Branch surface.*—Pubescent.

*Branch aspect.*—Lateral stems held upright to an average angle of 30° to vertical.

*Branch internode length.*—Average of 2.1 cm.

*Branching.*—1 main branch, 12 secondary branches.

Foliage description:

*Leaf shape.*—Narrowly elliptical to elliptical.

*Leaf division.*—Simple.

*Leaf base.*—Attenuate.

*Leaf apex.*—Acute.

*Leaf fragrance.*—None.

*Leaf venation.*—Pinnate, upper surface; matches leaf color, lower surface; 191B, mid- vein 145B.

*Leaf margins.*—Serrate.

*Leaf arrangement.*—Opposite.

*Leaf attachment.*—Petiolate.

*Leaf surface.*—Both surfaces are smooth, matte, and pubescent.

*Leaf size.*—Up to 8.8 cm in length and an average of 2.7 cm in width.

*Leaf quantity.*—An average of 12 per main stem.

*Leaf color.*—Young upper surface; 137B, mature upper surface; NN137B, young lower surface; 191C, mature lower surface; 191B.

*Petioles.*—An average of 4 mm in length and 2 mm in diameter, strong, surface slightly pubescent, color; 145B.

Inflorescence description:

*Inflorescence type.*—Compound terminal and axial panicles, held upright.

*Inflorescence size.*—Up to 7.2 cm in height, up to 6 cm in width.

*Flower fragrance.*—Sweet, pleasant and medium strength.

*Lastingness of flowers.*—An average of 5 days, persistent.

*Flower buds.*—Oblong in shape, average of 5 mm in length and 1 mm in diameter, color; 155C and 65C.

*Flower aspect.*—Upright, slightly outward.

*Flower quantity.*—Average of 300 flowers per inflorescence and 22 inflorescences.

*Flower type.*—Single, salverform.

*Flower surface.*—All surfaces glabrous and matte.

*Flower size*.—An average of 9 mm in height, 5 mm in diameter, flower throat; 3 mm in length, 1 mm in diameter, flower tube; 4 mm in length, 1 mm in diameter.

*Peduncles*.—Primary; an average of 1 cm in length and 3 mm in diameter, secondary; an average of 1 cm in length and 5 mm in diameter, 145B in color, strong, glossy and pubescent surface.

*Pedicels*.—An average of 2 mm in length and 1.5 mm in diameter, 145B in color, strong, surface is pubescent.

*Calyx*.—Campanulate in shape, an average of 2 mm in length and 1.5 mm in diameter.

*Sepals*.—4, 1 whorl, rotate arrangement, fused into a campanulate shape, 2 mm in length, <1 mm in width, lanceolate in shape, acute apex, fused base, entire margin, both surfaces are matte and slightly pubescent, color; when opening and fully open upper and lower surface 145B, flushed with 187A.

*Petals*.—Average of 4, rotate, fused into salverform, 1 whorl, roughly spatulate in shape, slightly undulate margin, rounded apex, an average of 3 mm in length and 2 mm in width, color: petals; young and mature upper and lower surface 62B, changing to 62C, throat; young and mature inside 25B, young and mature outside 32C, base N155D.

Reproductive organs:

*Gynoecium*.—4 pistils, 3 mm in length, style; an average of 2 mm in length, 145D in color, stigma; elongated, 1 mm in length and 145B in color, ovary is 145D in color.

*Androecium*.—Stamens; 4, filament; 4 mm in length, 25B in color, anther; ovate in shape, 1 mm in length, 11D in color, pollen; low in quantity, too little to measure color.

*Fruit and seed*.—No seeds or fruit observed to date.

It is claimed:

1. A new and distinct cultivar of *Buddleja* plant named 'Botex 011' as herein illustrated and described.

* * * * *